United States Patent [19]

Naser et al.

[11] Patent Number: 4,844,079
[45] Date of Patent: Jul. 4, 1989

[54] LITHOTRIPTER COMPRISING LOCATING APPARATUS

[75] Inventors: Georg Naser, Zirndorf; Helmut Reichenberger, Eckental, both of Fed. Rep. of Germany

[73] Assignee: Siemens Aktiengesellschaft, Berlin and Munich, Fed. Rep. of Germany

[21] Appl. No.: 108,018

[22] Filed: Oct. 14, 1987

[30] Foreign Application Priority Data

Oct. 23, 1986 [DE] Fed. Rep. of Germany ....... 3636093

[51] Int. Cl.$^4$ ............................................ A61B 17/22
[52] U.S. Cl. ............................ 128/660.03; 128/24 A; 128/328
[58] Field of Search ...................... 128/24 A, 328, 660

[56] References Cited

U.S. PATENT DOCUMENTS

| | | | |
|---|---|---|---|
| 3,954,098 | 5/1976 | Dick et al. ............................ | 128/661 |
| 4,539,989 | 9/1985 | Forssmann et al. ................. | 128/328 |
| 4,610,249 | 9/1986 | Makofski et al. .................... | 128/328 |
| 4,669,483 | 6/1987 | Hepp et al. ........................... | 128/660 |
| 4,674,505 | 6/1987 | Pauli et al. ............................ | 128/328 |
| 4,685,461 | 8/1987 | Forssmann et al. ................. | 128/328 |
| 4,705,026 | 11/1987 | Chaussy et al. .................... | 128/328 X |

FOREIGN PATENT DOCUMENTS

| | | |
|---|---|---|
| 0131653 | 1/1985 | European Pat. Off. . |
| 2722252 | 11/1978 | Fed. Rep. of Germany . |
| 3543867 | 6/1987 | Fed. Rep. of Germany ...... 128/328 |

*Primary Examiner*—Ruth S. Smith
*Attorney, Agent, or Firm*—Hill, Van Santen, Steadman & Simpson

[57] ABSTRACT

A lithotripter for treating calculi has a housing formed by a first sub-housing with an opening with a membrane for contacting the patient, a second sub-housing composed of two parts with the first of the two parts forming a cylindrical bearing with the first sub-housing to allow rotation around an axis, a second part being mounted for pivotal movement on an axis extending perpendicular to the axis of rotation. The second housing part supports the source of the shockwave to create a shockwave on a central axis and includes a focussing arrangement mounted on the second part for focussing the shockwave on the central axis. To locate the calculus or stone, two scanning heads having sector scanning planes are mounted at a predetermined angle on the focus arrangement. To locate the stone, the second housing part is rotated to locate the stone in one of the scan planes, and then the second housing part is pivoted to move the second scan plane onto the stone.

18 Claims, 3 Drawing Sheets

LITHOTRIPTER COMPRISING LOCATING APPARATUS

BACKGROUND OF THE INVENTION

The present invention is directed to a lithotripter or lithotripsy device comprising a focussing means for a shockwave pulse emitted along a central axis, said lithotripter having first and second ultrasound transmission and reception apparatuses, which are arranged adjacent a focussing means in a fixed, three-dimensional relationship to aid in positioning the calculi or stone to be disintegrated.

A lithotripter is disclosed in German publication No. 27 22 252. This publication discloses a device having a reflector in the form of a ellipsoid, which is provided as focussing means. Two ultrasound transducers are secured to the housing wall of the reflector. The ultrasound transducers are adjusted so that they intersect the second focal point of the ellipsoid at an angle of about 30°. The calculus or stone is identified according to the A-image method. In the exemplary embodiment described in the German application, the patient is arranged in a water bath so that displacement of the lithotripter does not involve any problems when coupling the shockwaves to the patient.

The situation is different when the lithotripter is coupled to the patient via a membrane and what is referred to as a "dry coupling", such as disclosed in U.S. Pat. No. 4,674,505, whose disclosure is incorporated by reference thereto and which patent claims priority from German Patent Application No. 33 28 051. When utilizing a "dry coupling", care must be exercised to see that the coupling membrane lies against the patient optimally unmodified during the locating procedure. Moreover, no difficulties should occur at a lithotripter when locating calculi in a complicated position, as can occur to a particular degree given, for example, gall stones.

U.S. Pat. No. 4,669,483, whose disclosure is incorporated by reference and which claims priority from German Patent Application No. 34 27 001, discloses a locating and positioning apparatus which works with an ultrasound resonator guided by a cardanic suspension. A three-dimensional spatial locating can be carried out here only with considerable outlay for the apparatus.

SUMMARY OF THE INVENTION

The object of the present invention is to provide a lithotripter of the above-known types, wherein complicated calculi positions can also be reliably spatially located without the condition and position of the coupling membrane at the patient having to be modified.

This object is inventively achieved in a lithotripter having a focussing means for a shockwave pulse emitted along a central axis, a first and a second ultrasonic transmission and reception means for locating the calculi being arranged in a fixed spatial relationship relative to the focussing means. The improvements are that the ultrasound transmission and reception means are constructed as sector scanners whose scanning planes describe a prescribed angle relative to one another and proceed through the central axis, that the first ultrasound transmission and reception means is rotatable around the central axis, and the second ultrasound transmission and reception means is movable therewith, said focussing means being mounted by means for displacement along the central axis and with said displacement means moving both the first and second ultrasonic transmission and reception means.

A particular advantage of the improvement lies in the ease in which the apparatus can be manipulated when locating a calculus, particularly a gall stone.

Other advantages and features of the invention will readily be apparent from the following description of the preferred embodiments, the drawings and claims.

DESCRIPTION OF THE PREFERRED EMBODIMENTS

Figure 1:
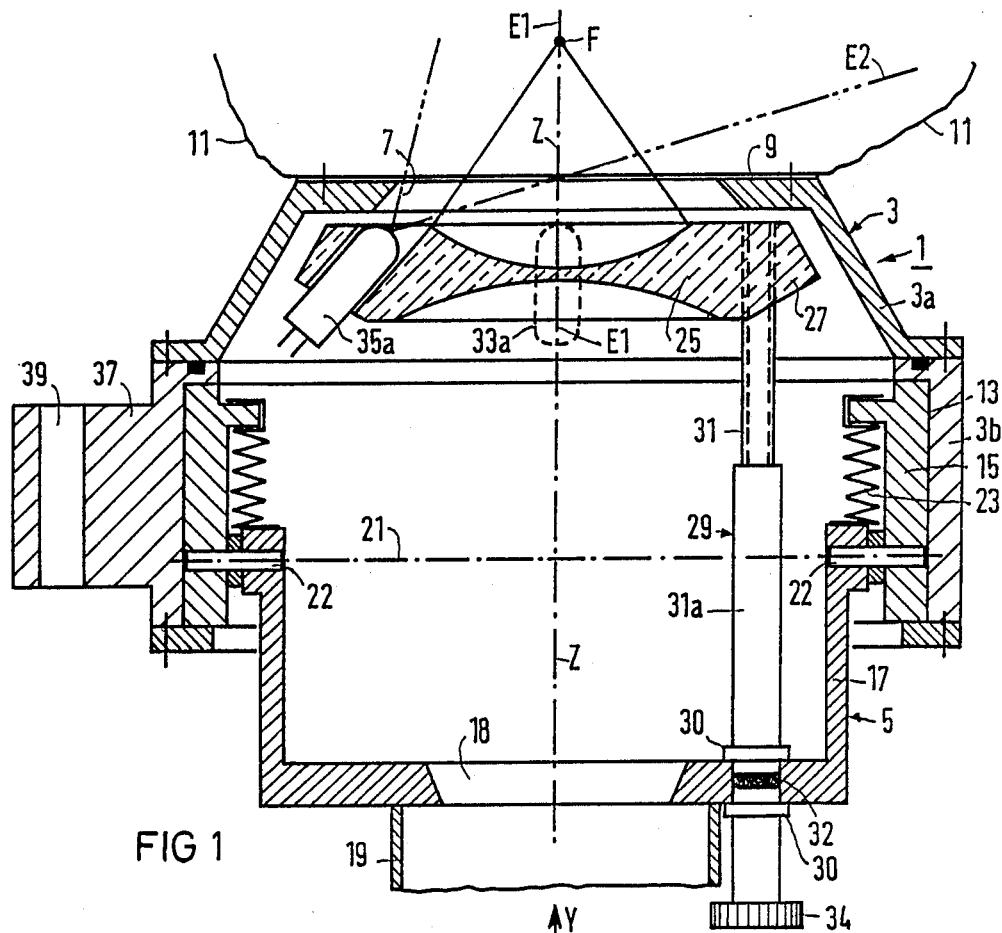
FIG. 1 is a cross sectional view through a lithotripter of the present invention having a focussing means and two ultrasound sector scanner means.

The principles of the present invention are particularly useful when incorporated in a lithotripter, generally indicated at 1 in FIG. 1. The lithotripter 1 is composed of a first sub-housing 3 and a second sub-housing 5, which are essentially rotationally symmetrical. The sub-housing 3 has an upper domed part 3a with a central opening 7, which is covered by a coupling membrane 9, which is over the opening. Shockwave pulses generated in the lithotripter 1 will emerge through this opening 7 via the coupling membrane 9 into a patient 11, which is to be treated. A lower, essentially annular part 3b of the first sub-housing 3, is rotatably connected to the second sub-housing 5 by a plain cylindrical bearing 13.

The second sub-housing 5 includes a non-pivotable upper or first part 15, which is fashioned as an annular member and whose outside surface is received by the part 3b to form the cylindrical bearing 13. The sub-housing 5 has a pivotable pot-shaped or second part 17, whose floor or base has an opening 18 on which a shockwave source 19 is secured. The shockwave source 19 can, preferably, be a shockwave tube, which is disclosed in greater detail in U.S. Pat. No. 4,674,505.

The pivotable pot-shaped part 17 is pivotably mounted to tilt around a swivel axis 21 by a pair of trunnions 22 which, as illustrated, lie in the plane of the paper in FIG. 1. The exact arrangement of the swivel axis 21 shall be set forth in greater detail hereinafter. In order to achieve a water-tightness of the lithotripter housing 3 and 5, the pivotable pot-shaped part 17 and the non-pivotable part 15 are interconnected to one another by an inwardly situated bellows 23. Given a pivot of the pot-shaped part 17, one half of the bellows 23 will be compressed, while the other half is pulled or stretched apart. A filling of the housing parts 3 and 5 with a dielectric, such as, for example, water, is required for reasons of the shockwave propagation.

The shockwave source 19 has a central axis Z, which coincides with the central axis of a focussing means 25, which is mounted in the housing parts 3 and 5 adjacent the membrane 9. The focussing means 25, as illustrated in the exemplary embodiment, is a biconcave lens. The convergent lens of the focussing means is arranged centrally relative to the central axis Z and is mounted for displacement along the central axis Z by displacement means 29. To this end, the displacement means comprises, for example, three rotating rods 31 (only one being shown for purposes of illustration in FIG. 1) having threads, which rods are offset by an angle of 120° relative to one another. The threads are cut into the upper part of the revolving rod 31, which is received in a lower part 31a of the revolving rod 31. The lower rod 31a is mounted in the floor or base of the part 17 in a rotationally movable fashion. Two respective locking rings 30 hold every rod 31 axially rigid with respect to the part 17. To provide a seal for the rod, an O-ring 32 is situated in an annular channel which is formed in the part 31a between the locking rings 30.

The edges of the revolving threads 31 engage into the inside threads at an outer edge 27 of the lens or focussing means 25. A uniform rotation of the three revolving threads 31 displaces the lens 25 along the central axis Z and, thus, perpendicular to the shockwave emission surface formed by the membrane 9. A gear wheel 34 is mounted on the ends of each of the three thread parts 31a to create this linear displacement. All three gear wheels 34 are driven by a common tooth belt (not shown), which is driven by a motor (not shown).

The lens 25 has a focal point F, which, thus, remains on the central axis Z during displacement.

The heads 33a and 35a of the two ultrasound transmission and reception means 33 and 35, respectively, are fashioned as sector scanners and are arranged on the edge 27 of the lens 25 with a relative offset to one another by a rigidly prescribed angle alpha with respect to the axis Z. In the illustrated embodiment, the angle alpha amounts to 90°. The first head 33a is shown in broken lines, since it is situated in front of the plane of the observation with respect to the cross section of FIG. 1. The scanning plane E1 of the first ultrasound transmission and reception apparatus 33 extends perpendicular to the plane of the paper and proceeds through the central axis Z.

The second scan plane E2, which is produced by the second sector scanner or head 35a of the second ultrasound transmission and reception means lies in the plane of the paper and is illustrated by lines including dashes and three dots. The second scan plane E2 also extends through the axis Z. The geometrical conditions for the scan planes E1 and E2, which extend perpendicular to one another and both extend through the central axis Z of the focussing means 25, are rigidly prescribed. The ultrasonic heads 33a and 33b are illustrated as being inclined towards the focal point F and are accommodated in the periphery or at the edge 27 of the lens 25 and are, thus, firmly mounted therein.

Three or four reinforcements or bulges 37 (only one is shown) are provided on the part 3b of the first sub-housing 3. Each of these bulges has a bore 39, which receives rods or members of a mounting means, which enable the lithotripter 1 to be moved into and out of engagement with the patient 11.

Figure 2:
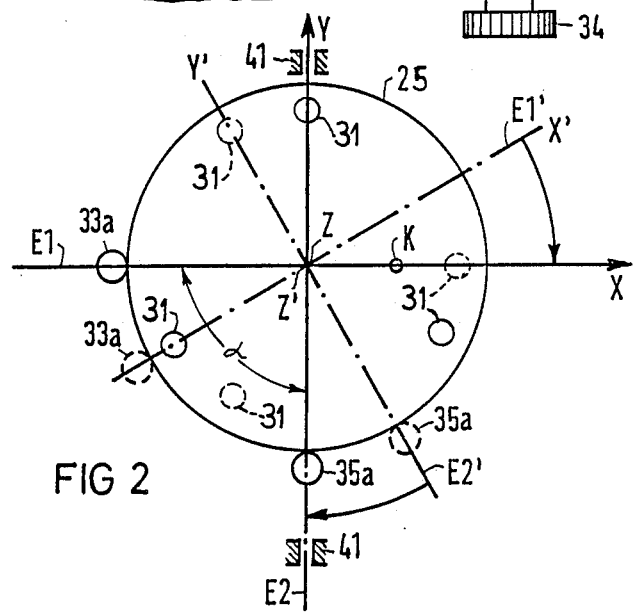
FIG. 2 is a diagrammatic presentation illustrating the step of bringing the first scan plane into congruence with a calculus or stone.

The process or method of locating the lithotripter 1 is illustrated in FIGS. 2–5. FIG. 2 illustrates a schematic plan view of the effective focussing means 25, as well as the first sector scanner 33a with its first scan plane E1 in the plane X-Z, and the second scanner head 35a with its second scan plane E2, which is in the plane Y-Z. In order to pivot the second scan plane E2 around the swivel axis 21 of FIG. 1, the Y axis is provided with a symbolic swivel bearing 41. The sector-shaped scan planes E1 and E2 can be viewed on a picture screen of the apparatus 33 or 35.

In broken lines, FIG. 2 shows a constellation of the axis X', Y' and Z', wherein Z' is identical to Z of the lithotripter 1 relative to a calculus K in the inside of the patient 11, as initially randomly derived when the lithotripter is coupled to the patient still undirected when first applied. The calculus or stone K lies at some location between the scan planes E1' and E2', which are not yet aligned.

As a first step for the exact location of the stone K in a lithotripter adjustment, the second sub-housing 5 is rotated around the central axis Z with the assistance of the cylindrical bearing 13 upon entrainment of both the apparatuses 33 and 35 until the calculus or stone K appears in the first scan plane E1 of the first ultrasonic scanner head 33. This corresponds to a solid line X, Y axis in FIG. 2. For the sake of clarity, the apparatus 33 and 35 are shown outside of the lens 25, however, in the present case, the overall arrangement of the lens 25, with the heads 35a and 33a are all rotated together.

Figure 3A:
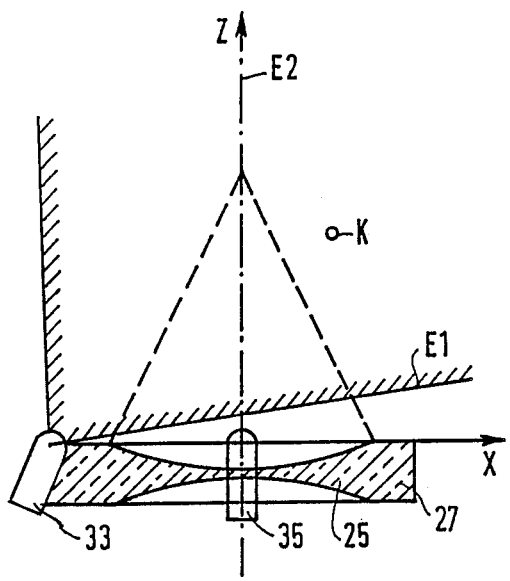
FIG. 3a is a diagrammatic cross sectional view along the first scanning plane showing the position of the second scanning plane relative to the calculi.
Figure 3B:
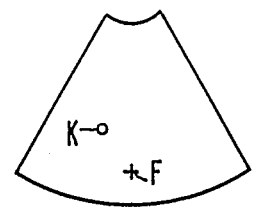
FIG. 3b is a diagrammatic view of the image on the picture screen for the second scanning plane.

With the stone or calculus K lying in the plane E1, the apparatus will have the configuration or cross section illustrated in FIG. 3a. The picture screen image of the calculus K and the mixed-in focus F occurs, as illustrated in FIG. 3b. However, the scan plane E2, which in FIG. 3a extends perpendicular to the plane of the paper through the axis Z, still misses the calculus or stone K. The picture screen for the second sector scanner 35, thus, does not yet show the calculus K.

Figure 4B:
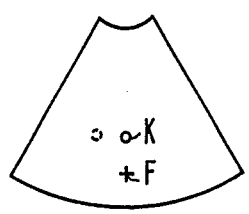
FIG. 4b is the image on the screen for the first scanning plane.
Figure 4A:
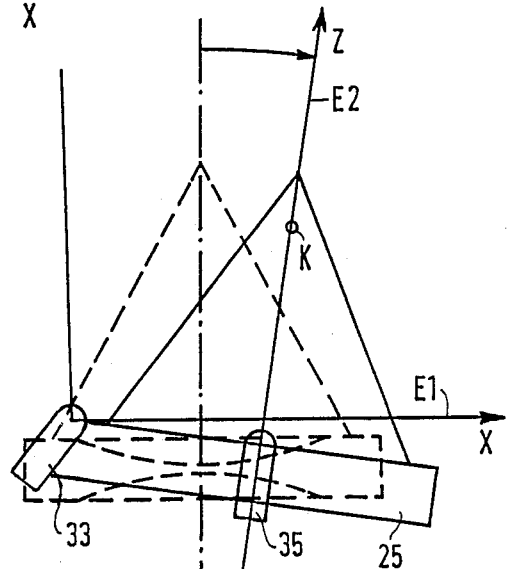
FIG. 4a is a diagrammatic view showing tilting on a tilting axis to locate the second plane on the calculi.

As illustrated in FIG. 4a, the next step is to pivot the shockwave source 19 and focussing means 25, plus the rigidly connected ultrasound transmission and reception apparatuses 33 and 35 around the swivel axis 21, which extends perpendicular to the plane of the paper from the position illustrated in broken lines to a position where the calculus K will lie in the plane E2 and will appear in the picture screen of the second sector scanner 35.

The swivel axis 21 is aligned so that the calculus or stone K simultaneously remains in the scan region of the first ultrasonic scanner 33a. This means that the axis 21 must be arranged to extend perpendicular to the central axis Z and must also lie in the scan plane E2 of the second ultrasonic scanner head 35a, which is imaged as lying in the back side of the focussing means 25.

Figure 4C:
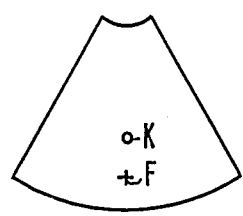
FIG. 4c is the image on the screen for the second scanning plane.

FIG. 4b is the image for the first sector scanner 33 with the position of the calculus K shown in broken lines before the pivoting and the position after pivoting is shown in bold lines. In FIG. 4c, the image for the sector scanner 35 illustrating the position of the calculi after the pivoting so that the calculi also lies in the plane E2. After the second positioning step, which is the step of pivoting on the axis 21, the lithotripter 1 is aligned so that the calculus or stone K lies on the central axis Z and, thus, can be seen on both picture screens.

The depth position of the calculus K on the central axis Z, however, has not coincided with the focal point F of the focussing means 25. The focal point F is now displaced towards the calculus K in a third adjustment step by turning the rotating threads or positioners 31 of the displacement means 29. The focussing procedure is, thus, concluded and the first shockwave pulses can now be triggered to disintegrate the stone K.

The displaceability of the focal point F, without having to modify the position of the coupling membrane 9 relative to the patient 11 is an advantage of the lithotripter of the present invention. The possibility of turning and/or swivelling the scanning planes E1 and E2 of the ultrasound scanners 33 and 35, respectively, creates the possibility of undertaking a reliable positioning, even given complicated calculus positions, which occurs particularly with gall stones.

The reliability to treatment is, thus guaranteed.

In the above description, it is assumed that the calculus was in a fixed position. However, movement of the stone will occur because of breathing activities, and this movement is a continual appearance and disappearance in the two ultrasound images. The same, to a lesser degree, will also occur due to the heart activity. It is, therefore, advantageous when the registration of the ultrasound image respectively occurs in the same respiration and/or each ECG position at which the shockwave is likewise to be triggered. It is just as advantageous for the evaluation carried out by the attending physician when only these ultrasound images are displayed.

Figure 5:
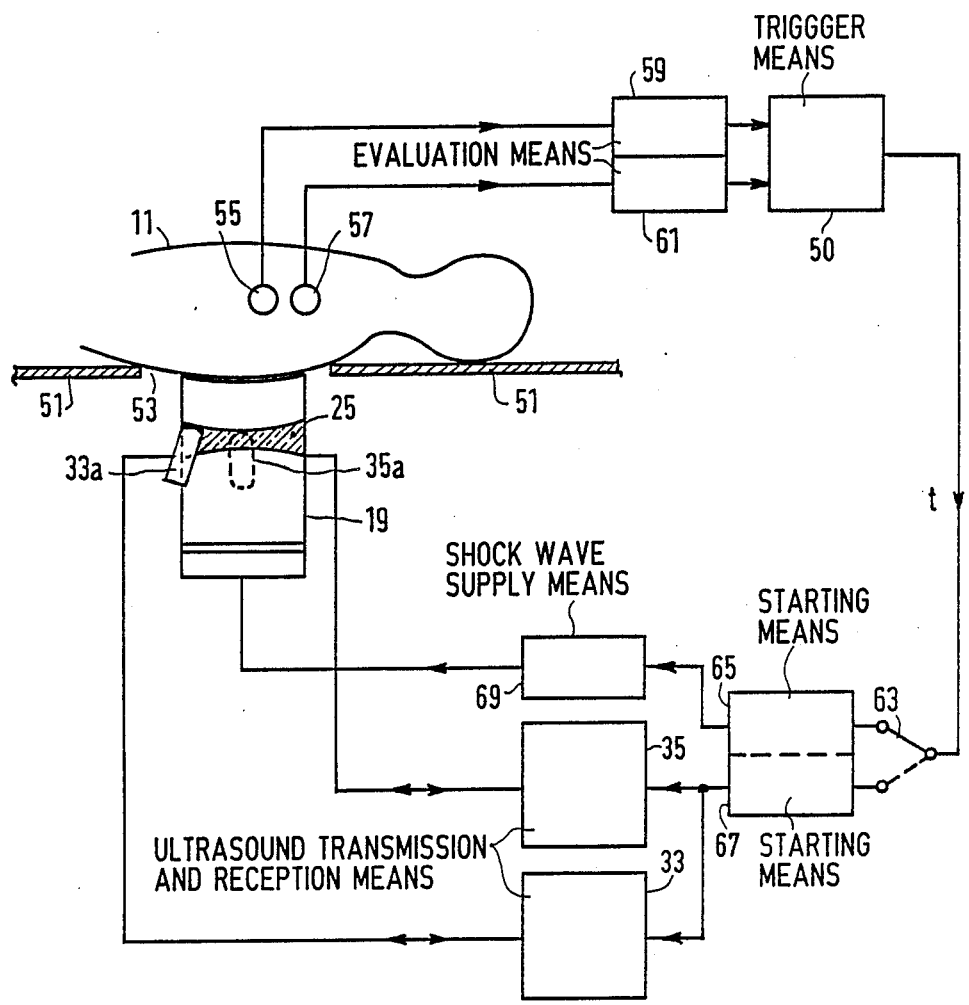
FIG. 5 is a schematic diagram of the triggering system for both the scanning means and the shockwave transducer for the lithotripter in accordance with the present invention.

In FIG. 5, a common trigger mechanism or means 50 is provided for this purpose. This trigger mechanism is used both during the registration for the ultrasound images, as well as when triggering the shockwaves. To this end, a pickup or sensor 55 for the respiration and a pickup or sensor 57 for the heart activity (ECG) are arranged on the patient 11, who is positioned on a patient supporting plate 51. As illustrated, the plate 51 has an opening 53, through which the lithotripter extends to apply the shockwaves to the patient. The output signal of the sensors 55 and 57 are supplied to correspondingly known evaluation devices or means 59 and 61, respectively. The output signals of these evaluation devices or means are conducted in common to a trigger mechanism 50 in the present installation. It is adequate in many uses to only provide the one sensor 55 with its evaluation means or device 59 for supervising respiration and to omit the sensor, such as 57, and its evaluation means 61 for heart activity.

In a known way, the trigger mechanism 50 forms a trigger signal t from the supplied signals, and this trigger signal t is then supplied via a selective switch 63, either to a trigger mechanism or starting means 65 for the shockwaves, or to an exposure starting means 67 for the ultrasound images. In the illustrated switch position, the shockwave supply or generator means 69, which belongs to the shockwave source 19, is driven with the trigger signal t. In the present case, the shockwave source 19 is shown as a known shockwave tube.

In the other non-illustrated position of the switch 63, the trigger signal t charges the exposure starting means or mechanism 67 for the ultrasound images of the two ultrasound scanners 33 and 35. The echo signals picked up by the heads 33a or, respectively, 35a are portrayed on the picture screens (not shown) with the assistance of the apparatus or means 33 and 35, respectively. According to the arrangement of FIG. 5, the registration of the two ultrasound images respectively occurs in a respiratory position in which the shockwave will also be subsequently triggered. As explained, this can also apply to phase relationship of the heart activity.

Although various minor modifications may be suggested by those versed in the art, it should be understood that we wish to embody within the scope of the patent granted hereon all such modifications as reasonably and properly come within the scope of our contribution to the art.

We claim:

1. In a lithotripter having a source for emitting a shockwave pulse and means for focussing the shockwave pulse along a central axis, said lithotripter including first and second ultrasonic transmission and reception means being arranged on the focussing means in a fixed spatial relationship, the improvements comprising both ultrasonic transmission and reception means being constructed as sector scanners having scanning planes, said scanning planes describing a prescribed angle with one another and proceeding through the central axis, and mounting means for supporting the first and second ultrasonic transmission and reception means for movement around the central axis, said mounting means including displacement means for moving the means for focussing along the central axis with movement of at least a portion of each of said first and second ultrasonic transmission and reception means, said mounting means providing means to enable swivelling of the means for focussing and said portions of the first and second ultrasound transmission and reception means around a swivel axis extending perpendicular to the central axis and lying in the same plane as the scanning plane of the second ultrasonic transmission and reception means.

2. In a lithotripter according to claim 1, wherein the angle between the two scanning planes is 90°.

3. In a lithotripter according to claim 1, wherein the focussing means is a lens on which said portion of both of the ultrasound transmission and reception means are secured.

4. In a lithotripter according to claim 1, wherein the mounting means includes a member having an opening covered by a coupling membrane and said mounting means mounts the focussing means adjacent to said coupling membrane.

5. In a lithotripter according to claim 4, wherein the mounting means comprises a housing having a first sub-housing including the member with the coupling membrane and a second sub-housing supporting the shockwave source.

6. In a lithotripter according to claim 5, wherein both sub-housings are mounted for rotatable relationship to one another by means of a cylindrical bearing.

7. In a lithotripter according to claim 6, wherein the second sub-housing has a non-pivotable first part forming a portion of the cylindrical bearing with the first sub-housing and a second part mounted for pivotable movement on said swivel axis relative to the first part, said second part having a base on which the shockwave source is mounted and said first and second parts being interconnected by a bellows.

8. In a lithotripter according to claim 7, wherein said bellows forms a liquid-tight connection between said first and second parts so that the first and second sub-housing form a liquid-tight chamber for receiving a liquid dielectric.

9. In a lithotripter according to claim 7, wherein the displacement means for the focussing means is mounted on the second part of the second sub-housing.

10. In a lithotripter according to claim 9, wherein the displacement means comprises threaded members.

11. In a lithotripter according to claim 1, which includes means for an equiphase ultrasound image registration and shockwave triggering.

12. In a lithotripter according to claim 11, wherein the means for equiphase ultrasound image registration and shockwave triggering includes means for sensing patient conditions, selected from respiration states and ECG.

13. In a lithotripter according to claim 12, wherein the means for equiphase ultrasound image registration and shockwave triggering includes a common triggering mechanism for actuating the ultrasound image registration, as well as the shockwave triggering at a respectively same respiratory position.

14. In a lithotripter according to claim 1, wherein the portions of the ultrasound transmission and reception means are positioned on an edge of the focussing means.

15. In a lithotripter having a housing, means for generating a shockwave pulse mounted on said housing, means for focussing the shockwave pulse along a central axis, a first and second means for ultrasound transmission and reception being mounted in said housing with portions on the focussing means in a fixed, spatial relationship, the improvement comprising both the first and second means for ultrasound transmission and reception being constructed as sector scanners having scan planes describing a prescribed angle with one another and proceeding through the central axis, said housing having a first sub-housing and a second sub-housing, said second sub-housing having first and second parts, said first part of the second sub-housing and said first sub-housing forming a cylindrical bearing to enable rotation of the second sub-housing around the central axis relative to the first sub-housing, said second part mounted for pivotal movement in the first part around a pivot axis extending perpendicular to the central axis, said means for generating a shockwave pulse being mounted on the second part, mounting means for mounting the focussing means on said second part for movement therewith and the scan plane of the second means being in the same plane as the pivot axis, said mounting means including means for displacing the focussing means and at least an ultrasound head of each of said first and second means along the central axis so that the focus point for the shockwave is positioned on a stone by first rotating the second sub-housing until the scan plane of the first means coincides with the stone to be located, then pivoting the second part to move the second scan plane to lie on said stone and subsequently displacing the focussing means to move the focus point for the shockwaves to lie on the stone.

16. In a lithotripter according to claim 15, wherein the first sub-housing has an opening covered by a coupling membrane and said means for mounting the focussing means positions the focussing means adjacent said membrane.

17. In a lithotripter according to claim 16, wherein the first and second parts of the second sub-housing are interconnected by a bellows to provide a fluid-tight chamber formed by the first and second sub-housings for receiving a coupling fluid.

18. In a lithotripter having shockwave means for emitting a shockwave pulse and means for focussing the shockwave pulse along a central axis, said lithotripter including first and second means for ultrasonic transmission and reception being arranged on the focussing means in a fixed spatial relationship, the improvements comprising said focussing means being a lens, both the first and second means being constructed as sector scanners with a scanner head and scanning plane, at least said scanner heads being mounted on the lens with the scanning planes describing a prescribed angle with one another and proceeding through the central axis, and mounting means for supporting the lens and the scanning head of the first and second means for movement around the central axis, said mounting means including displacement means for moving the lens with the scanner heads along the central axis relative to the shockwave means, said mounting means providing means to enable swivelling of the second means around a swivel axis extending perpendicular to the central axis and lying in the plane of the scanning plane of the second means.

* * * * *